US00PP29099P2

(12) United States Plant Patent
Eveleens

(10) Patent No.: US PP29,099 P2
(45) Date of Patent: Mar. 13, 2018

(54) ***HYDRANGEA* PLANT NAMED 'HORT 10-087-01'**

(50) Latin Name: *Hydrangea macrophylla*
Varietal Denomination: Hort 10-087-01

(71) Applicants: Horteve Breeding BV, De Kwakel (NL); Kolster Holding BV, Boskoop (NL)

(72) Inventor: Cornelis Pieter Eveleens, De Kwakel (NL)

(73) Assignees: HORTEVE BREEDING B.V., Aalsmeer (NL), part interest; KOLSTER HOLDING B.V., Boskoop (NL), part interest ( * ) Notice: Subject to any disclaimer, the term of this patent is extended or adjusted under 35 U.S.C. 154(b) by 0 days.

(21) Appl. No.: 15/330,657

(22) Filed: Oct. 24, 2016

(51) Int. Cl.
*A01H 5/00* (2006.01)

(52) U.S. Cl.
USPC ..... Plt./250

(58) Field of Classification Search
USPC ..... Plt./226, 250
See application file for complete search history.

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of *Hydrangea macrophylla* plant named, 'Hort 10-087-01', that is characterized by its compact plant habit, its double sterile flowers with a large number of sepals that are deep pink in color, and its rounded star-shaped sterile flowers comprised of sepals with pointed tips.

2 Drawing Sheets

CROSS REFERENCE TO A RELATED APPLICATION

This application is co-pending with U.S. Plant Patent Applications filed for plants derived from the same breeding program that are entitled *Hydrangea* Plant Named 'Hort 10-087-07' (U.S. Plant patent application Ser. No. 15,330,659) and *Hydrangea* Plant Named 'HORT 10-080-01' (U.S. Plant patent application Ser. No. 15,330,660).

Botanical classification: *Hydrangea macrophylla.*

Varietal denomination: 'Hort 10-087-01'.

BACKGROUND OF THE INVENTION

The present invention relates to a new and distinct cultivar of *Hydrangea macrophylla* and will be referred to hereafter by its cultivar name, 'Hort 10-087-01'. 'Hort 10-087-01' represents a new bigleaf *hydrangea*, a perennial shrub grown for landscape use.

'Hort 10-087-01' was derived from an ongoing controlled breeding program directed by the Inventor. The objectives of the breeding program include developing new cultivars of *Hydrangea* with double flowers combined with compact plant habits and floriferous blooming habits. 'Hort 10-087-01' arose from a controlled cross made by the Inventor in Boskoop, The Netherlands in June of 2009 between unnamed and unpatented proprietary plants in the Inventor's breeding program; reference no. 08-022-08 (not patented) as the female parent and reference no. 08-022-06 (not patented) as the male parent. 'Hort 10-087-01' was selected as a single unique plant from amongst the resulting seedlings in June of 2014.

Asexual propagation of the new cultivar was first accomplished by stem cuttings by the Inventor in Boskoop, The Netherlands in July of 2011. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Hort 10-087-01' as a unique cultivar of *Hydrangea macrophylla.*

1. 'Hort 10-087-01' exhibits a compact plant habit.
2. 'Hort 10-087-01' exhibits double sterile flowers with a large number of sepals that are deep pink in color.
3. 'Hort 10-087-01' exhibits rounded star-shaped sterile flowers comprised of ovate-shaped sepals with pointed tips.

Both the female and male parent of 'Hort 10-087-01' differ from 'Hort 10-087-01' in being lacecap type *hydrangeas* and in having single flowers. 'Hort 10-087-01' can be most closely compared to the *Hydrangea macrophylla* cultivars 'Hort 10-087-07' (copending U.S. Plant patent application Ser. No. 15/330,659) and 'Youme H1917' (U.S. Plant Pat. No. 24,755). 'Hort-10-087-07' is similar to 'Hort 10-087-01' in having star-shaped, double sterile flowers. 'Hort 10-087-07' differs from 'Hort 10-087-01' in having flowers that are lighter pink in color, in having sterile flowers with longer sepals, and in having a less compact plant habit. 'Youme H1917' is similar to 'Hort 10-087-01' in having double flowers that are pink in color. 'Youme H1917' differs from 'Hort 10-087-01' in having sterile flowers that are more rounded with sepals that are orbicular in shape, and lighter pink in color.

BRIEF DESCRIPTION OF THE DRAWINGS

The accompanying colored photographs illustrate the overall appearance and distinct characteristics of the new

*Hydrangea*. The photographs were taken of a plant two years in age as grown in a 4-liter container outside under a shade screen in Boskoop, The Netherlands.

Figure 1:
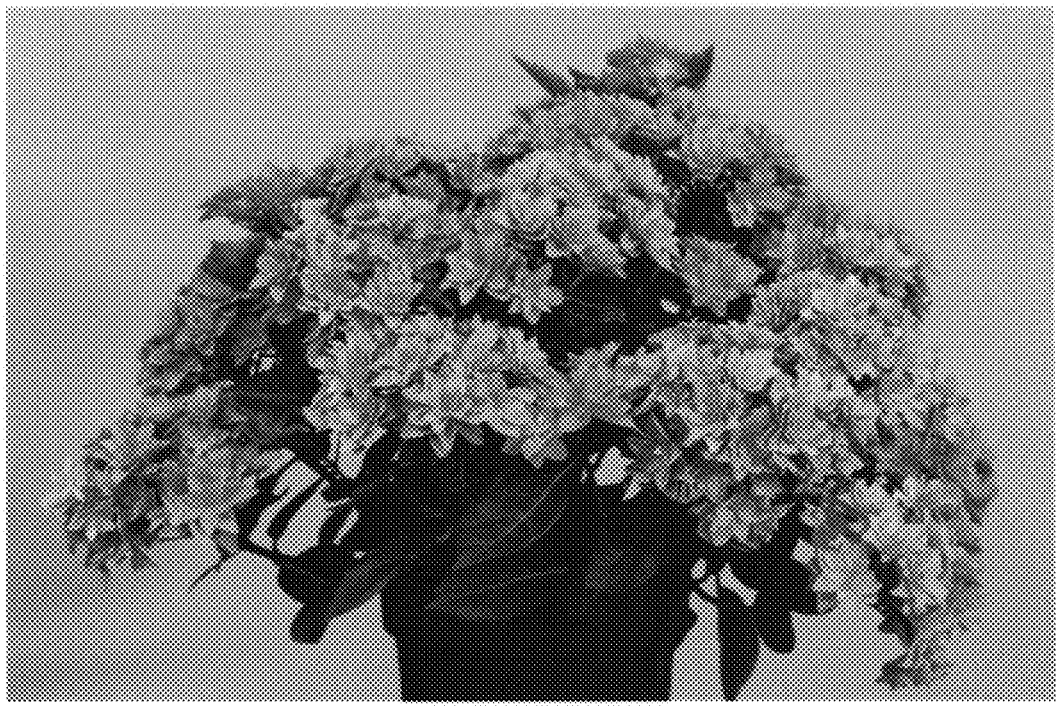

The photograph in FIG. 1 provides a side view of the plant habit of 'Hort 10-087-01' in bloom.

Figure 2:
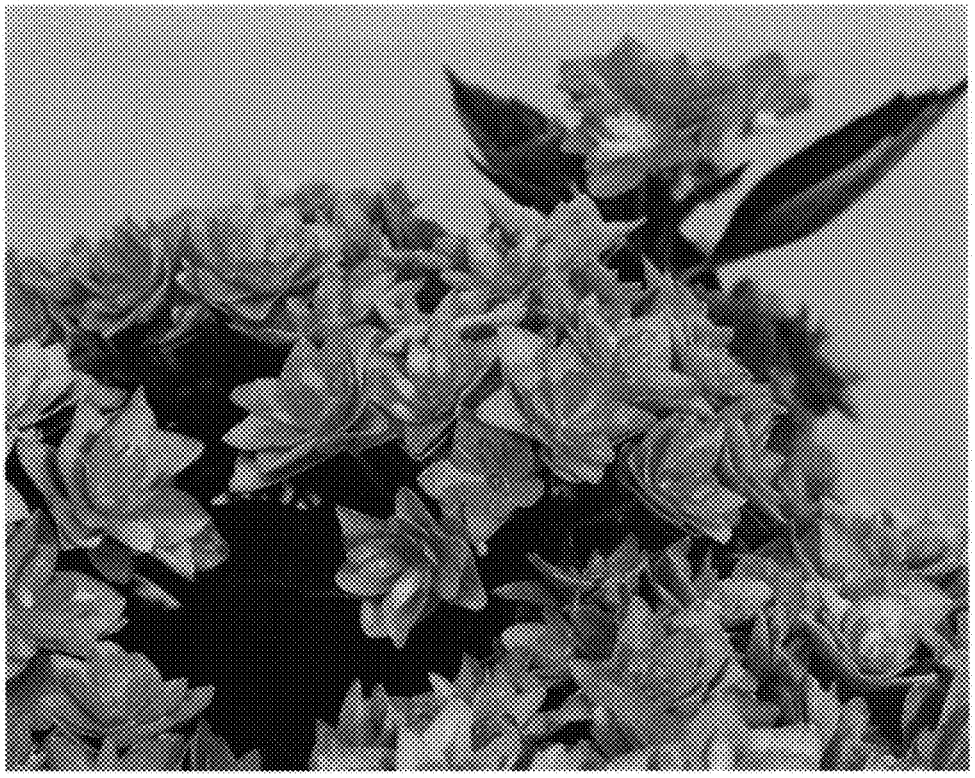

The photograph in FIG. 2 provides a close-up view of the inflorescences of 'Hort 10-087-01'.

Figure 3:
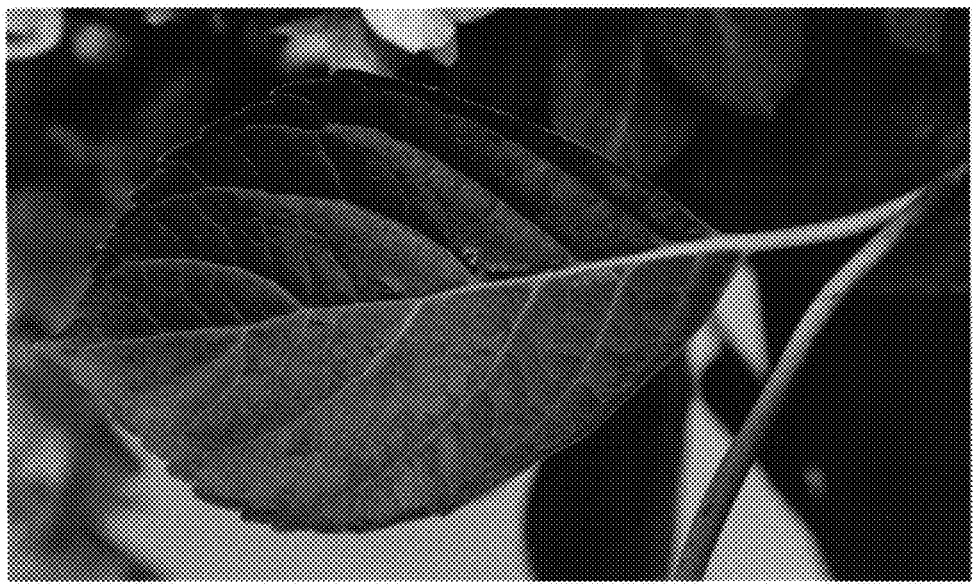

The photograph in FIG. 3 provides a close-up view of a leaf of 'Hort 10-087-01'.

The colors in the photographs are as close as possible with the photographic and printing technology utilized and the color values cited in the detailed botanical description accurately describe the colors of the new *Hydrangea*.

BOTANICAL DESCRIPTION OF THE PLANT

The following is a detailed description of plants two years in age as grown in 4-liter containers outside under a shade screen in Boskoop, The Netherlands. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period.*—From May to July in a greenhouse and from July to September outside in The Netherlands.

*Plant type.*—Perennial shrub, mophead-type *hydrangea.*

*Plant habit.*—Mounded and compact.

*Height and spread.*—Up to 1 m in height and 1.5 m in spread.

*Hardiness.*—At least in U.S.D.A. Zones 5 to 9.

*Diseases and pests.*—No susceptibility and resistance to pests and diseases has been observed.

*Root description.*—Fibrous and fine, 199D in color.

*Propagation.*—Stem cuttings.

*Time required for root development.*—An average of 3.5 weeks for root initiation with a young rooted plant produced in an average of six months.

*Growth rate.*—Moderate.

Stem description:

*Stem shape.*—Rounded.

*Stem strength.*—Strong.

*Stem aspect.*—Upright to an average angle of 45° to soil.

*Stem color.*—Immature and mature stems; 143C suffused with a blend between N186A and 200A at the internodes, older bark; 199C to 199D.

*Stem size.*—An average of 17.8 cm (excluding the inflorescence) in length and 5 mm in diameter.

*Stem surface.*—Immature and mature stems; glabrous, glossy, and moderately lenticellate with lenticels; elliptic in shape, an average of 2 mm in length and 0.75 mm in width, and a blend between N186A and 200A in color.

*Branching.*—Well-branched with an average of 27 lateral branches, branching improves with pinching.

*Internode length.*—An average of 3.9 cm.

Foliage description:

*Leaf shape.*—Broadly ovate to broadly obovate.

*Leaf arrangement.*—Opposite.

*Leaf division.*—Simple.

*Leaf number.*—An average of 4 (2 pairs) per lateral branch.

*Leaf base.*—Rounded to cuneate.

*Leaf apex.*—Apiculate.

*Leaf margins.*—Lower half of leaf blade; entire, upper half of leaf blade; serrate.

*Leaf venation.*—Pinnate, color; upper surface 144C and lower surface 145B to 145C.

*Leaf size.*—An average of 9.3 cm in length and 6.0 cm in width.

*Leaf attachment.*—Petiolate.

*Leaf surface.*—Upper surface; glabrous, slightly glossy, and moderately rugose, lower surface; glabrous, very slightly glossy, and moderately rugose.

*Leaf color.*—Young leaves; upper surface 143A and lower surface 146B, mature leaves; upper surface a blend between 139A and 141A and lower surface 147B.

*Petioles.*—Flattened, an average of 2 cm in length and 3.5 mm in width, color; upper and lower surfaces 144D, both surfaces; glabrous, smooth, and moderately glossy.

Inflorescence description:

*Inflorescence type.*—Flattened globular, mophead, compound corymb of rotate-shaped double sterile flowers.

*Lastingness of inflorescence.*—Sterile flowers; an average of 6 weeks, persistent, fertile flowers; an average of 3 weeks, persistent.

*Inflorescence number.*—One per lateral stem.

*Inflorescence size.*—An average of 11.3 cm in height and 15.9 cm in diameter.

*Flower number.*—An average of 44 sterile flowers and 36 fertile flowers per inflorescence.

*Flower fragrance.*—None.

*Flower aspect.*—Sterile flowers; upright to outwards and drooping, fertile flowers; upright.

*Flower size.*—Sterile flowers; an average of 5.4 cm in diameter and 3.1 cm in depth, fertile flowers; an average of 6 mm in diameter and 7 mm in depth.

*Flower shape.*—Sterile; rotate and double, fertile flowers; do not open, remain in the bud stage.

*Flower buds.*—Sterile flowers; an average of 9 mm in length and 6 mm in diameter, ovate in shape, color; 63A to 63B, fertile flowers; an average of 5 mm in length and diameter, broadly obovate in shape, color; 59D, fading to 143C in the bud stage.

*Peduncles.*—An average of 4 cm in length and 3 mm in diameter, held upright to outwards, 143C to 143D in color, glabrous and smooth surface, strong.

*Pedicels.*—Sterile flowers; an average of 3.8 cm in length and 1.5 mm in diameter, held at an average angle of 32.5° to peduncle, 68B in color, strong strength, very slightly glossy, smooth, glabrous surface, fertile flowers; an average of 5 mm in length and 0.75 mm in diameter, held at an average angle of 25° to peduncle, 144A in color, moderate strength, slightly glossy, smooth, and glabrous surface.

*Petals.*—Sterile and fertile flowers; not present.

*Sepals.*—Sterile flowers; an average of 21, arrangement; rotate and double in four whorls, elliptic to narrow obovate in shape, cuneate base, bluntly acute apex, entire margin, an average of 2.5 cm in length and 1.6 cm in width, color; upper surface when opening 61B, lower surface when opening 63B, upper surface when fully open 63B, lower surface when fully open 70C, color fades to 146D suffused with 63B on the upper surface and 146D on the lower surface, upper surface; glabrous, dull, and slightly velvety, lower surface; glabrous and dull, fertile flowers; an average of 10, rotate in arrangement, ovate in shape, acute apex, cuneate base, serrate margin, an average of 4 mm in length and 2 mm in width, color; upper and lower surfaces when opening and when fully open 144B, color does not fade, both surfaces smooth and glabrous.

Reproductive organs:

*Gynoecium.*—Sterile flowers; an average of 3 pistils, an average of 1 mm in length, stigma; club-shaped and 157D in color, style; 0.5 mm in length and 157A in color, ovary is 144C in color, fertile flowers; an average of 3, an average of 1 mm in length, stigma; club-shaped and 157D in color, style; 0.5 mm in length and 157A in color, ovary is 144C in color.

*Androecium.*—Sterile and fertile flowers; not present.

*Fruit and seed.*—No seeds or fruit observed.

It is claimed:

1. A new and distinct cultivar of *Hydrangea* plant named 'Hort 10-087-01' substantially as herein illustrated and described.

* * * * *